US00PP25187P3

(12) United States Plant Patent
Tsukahara

(10) Patent No.: US PP25,187 P3
(45) Date of Patent: Dec. 23, 2014

(54) ***PETUNIA* PLANT NAMED 'PBLYG39-0'**

(50) Latin Name: ***Petunia* hybrid**
Varietal Denomination: PBLYG39-0

(71) Applicant: Jun Tsukahara, Fukuoka (JP)

(72) Inventor: Jun Tsukahara, Fukuoka (JP)

(73) Assignee: Suntory Flowers Ltd (JP)

( * ) Notice: Subject to any disclaimer, the term of this patent is extended or adjusted under 35 U.S.C. 154(b) by 113 days.

(21) Appl. No.: 13/815,143

(22) Filed: Jan. 31, 2013

(65) Prior Publication Data

US 2014/0215670 P1 Jul. 31, 2014

(51) Int. Cl.
*A01H 5/00* (2006.01)

(52) U.S. Cl.
USPC ..... Plt./356.13

(58) Field of Classification Search
USPC ..... Plt./356.13
See application file for complete search history.

*Primary Examiner* — Susan McCormick Ewoldt
(74) *Attorney, Agent, or Firm* — Cassandra Bright

(57) ABSTRACT

A new and distinct *Petunia* cultivar named 'PBLYG39-0' is disclosed, characterized by a unique flower color of yellow with a soft pink margin, compact plants and abundant flowering. The new variety is a *Petunia,* suitable as an outdoor garden or container plant.

2 Drawing Sheets

Figure 1:
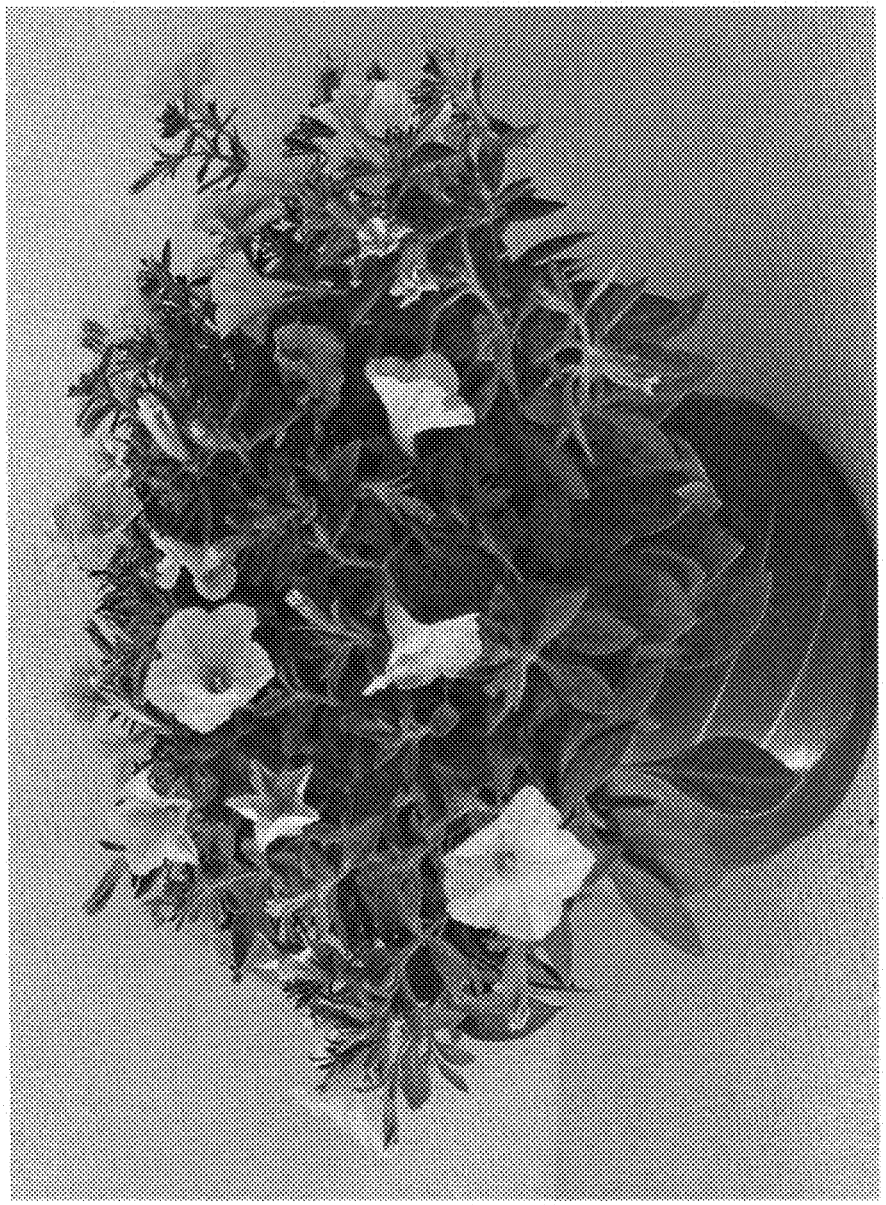

Latin name of the genus and species: *Petunia* hybrid.
Variety denomination: 'PBLYG39-0'.

The new *Petunia* cultivar resulted as part of a planned breeding program by the inventor Jun Tsukahara, in Yame, Fukuoka, Japan. The objective of the breeding program was to develop new *Petunia* varieties with interesting colors and attractive plant forms.

The new variety resulted from the crossing of the seed parent, an unnamed, unpatented proprietary *Petunia* seedling with the pollen parent, an unnamed, unpatented proprietary *Petunia* seedling in September of 2008. The new variety was discovered in May of 2009 by the inventor in a group of seedlings resulting from that crossing, in a commercial greenhouse in Yame, Fukuoka, Japan.

Asexual reproduction of the new cultivar 'PBLYG39-0' by vegetative cuttings was first performed at a commercial greenhouse in Yame, Fukuoka, Japan in May of 2009. Subsequently one generation has been produced and has shown that the unique features of this cultivar are stable and reproduced true to type.

SUMMARY OF THE INVENTION

The cultivar 'PBLYG39-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'PBLYG39-0.' These characteristics in combination distinguish 'PBLYG39-0' as a new and distinct *Petunia* cultivar:

1. Unique flower color with a yellow center and soft pink colored margins.
2. Very compact plant habit.
3. Abundant flowering.

COMPARISON TO THE PARENT VARIETIES

Plants of the new cultivar 'PBLYG39-0' are similar in most horticultural characteristics to plants of the unnamed proprietary seed parent. However, the new cultivar has a compact plant habit and smaller plants size compared to the creeping plant habit of the seed parent. Additionally, plants of the seed parent produce lavender with yellow eye colored flowers, whereas 'PBLYG39-0' produces flowers that are pink with yellow eye.

Plants of the new cultivar 'PBLYG39-0' are similar in most horticultural characteristics to plants of the unnamed proprietary pollen parent. However, the pollen parent produces pale yellow colored double flowers, whereas the new variety produces flowers that are pink with a yellow eye. Additionally, the new variety produces smaller flowers than the pollen parent.

COMPARISON TO COMMERCIAL VARIETIES

The new cultivar can be compared to the patented commercial variety 'Daiichi Bluette Purple2' U.S. Plant Pat. No. 22,236. 'PBLYG39-0' is similar to this commercial variety in most horticultural characteristics, most specifically, in plant habit, however, plants of the new cultivar produce pink flowers with a yellow center, compared to the solid red-purple flowers of 'Daiichi Bluette Purple2'.

The new cultivar can be compared to the patented commercial variety 'Bluette Gradation Pink' U.S. Plant Pat. No. 22,237. 'PBLRS38-0' is similar to this commercial variety in most horticultural characteristics, however, plants of the new cultivar are most compact. Additionally the new cultivar produces a larger flowers, with a softer pink outer margin coloration.

BRIEF DESCRIPTION OF THE PHOTOGRAPH

The accompanying photograph in FIG. 1 illustrates in full color typical flowers and foliage of 'PBLYG39-0'.

Figure 2:
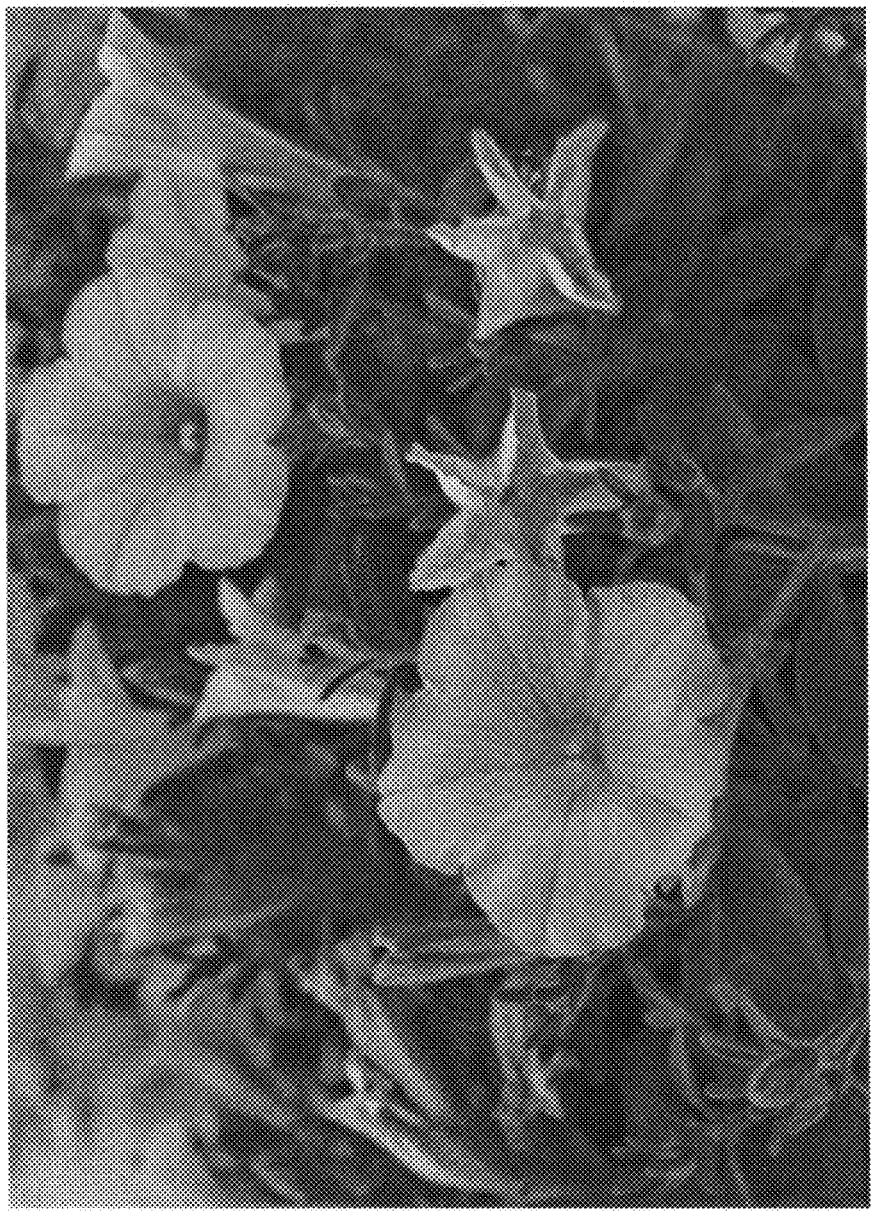

FIG. 2 illustrates a close up of the flowers of 'PBLYG39-0' grown in a greenhouse, in a 10 inch commercial basket. Age of the plant photographed is approximately 20 weeks from 5 rooted cuttings.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurement describe 'PBLYG39-0' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types. Botanical classification: *Petunia* hybrid 'PBLYG39-0'.

PROPAGATION

Time to intiate roots: About 7 days at approximately 25° C.
Time to develop roots: About 14 to 21 days at approximately 25° C.
Root description: Fine, fibrous.

PLANT

Growth habit: Mounding.
Age of the plant described: Approximately 20 weeks from 5 rooted cuttings.
Pot size of plant described: 10 inch basket.
Height: Approximately 18 cm from soil line to top of plant.
Plant spread: Approximately 48 cm at widest point.
Growth rate: Rapid.
Branching characteristics: Free branching.
Length of primary lateral branches: Approximately 15 cm.
Quantity of primary lateral branches: Approximately 60.
Characteristics of primary lateral branches:
- *Diameter.*—Approximately 0.3 cm.
- *Color.*—Near RHS Green 143C.
- *Texture.*—Highly pubescent. Somewhat sticky.
- *Strength.*—Highly flexible, moderately strong.

Internode length: Average range 0.6 to 1.8 cm.

FOLIAGE

Leaf:
- *Arrangement.*—Opposite.
- *Quantity.*—Approximately 12 per main lateral branch.
- *Average length.*—Approximately 5.0 cm.
- *Average width.*—Approximately 1.5 cm.
- *Shape of blade.*—Obovate.
- *Apex.*—Acute.
- *Base.*—Broadly attenuate.
- *Margin.*—Entire.
- *Appearance of top surface.*—Matte.
- *Appearance of top surface.*—Matte.
- *Pubescence.*—Very short, less than 1 mm hairs, densely covering top and bottom leaf surfaces.
- *Aspect.*—Very slightly upwardly curved.
- *Color.*—Young foliage upper side: Near RHS Green 137A. Young foliage under side: Near RHS Green 138C. Mature foliage upper side: Near RHS Green 137B. Mature foliage under side: Near RHS Green 137C.
- *Venation.*—Type: Pinnate. Venation color upper side: Near RHS Green 143C. Venation color under side: Near RHS Yellow-Green 144B.
- *Petiole.*—Length: Approximately 1.0 cm. Diameter: Approximately 0.2 cm. Color: Near RHS Yellow-Green 144B. Texture: Pubescent.

FLOWER

Natural flowering season: Spring and Summer.
Days to flowering from rooted cutting: Approximately 50.
Inflorescence and flower type and habit: Single salverform with fused petals.
Rate of flower opening: Approximately 2 to 3 days from bud to fully opened flower.
Flower longevity on plant: Approximately 1 week.
Approximate quantity of flowers per plant: Approximately 80 flowers and buds.
Flowers persistent:
Bud:
- *Shape.*—Oblong.
- *Length.*—Approximately 3.5 cm.
- *Diameter.*—Approximately 1.0 cm.
- *Color.*—Near RHS Yellow-Green 145C, flushed Green-Yellow 1B, distal end near Greyed-Red 181D.

Flower size:
- *Diameter, widest point.*—Approximately 4.5 cm.
- *Overall length.*—Approximately 3.2.
- *Flower tube length.*—Approximately 2.3 cm.
- *Flower tube diameter at distal end.*—Approximately 1.0 cm.
- *Flower tube diameter at proximal end.*—Approximately 0.4 cm.

Petals:
- *Length from throat.*—About 2.2 cm.
- *Width.*—About 1.8 cm.
- *Quantity.*—5, fused.
- *Texture.*—Smooth.
- *Apex.*—Mucronate.
- *Margin.*—Irregular, shallow, undulating crenations.

Color:
- *When opening.*—Inner surface: Inner tube near Yellow 11A, small transition area near petals close to Red 37A, thick margin near Red-55B, very edge of margin near Red-Purple 63C. Faint veins throughout near Yellow-Green 145B. Outer surface: Near Yellow-Green 145B, with thick, margin ring near Greyed-red 181D. Vein coloration near Yellow-Green 145B.
- *Fully opened.*—Inner surface: Petal base near Yellow 10B, main petal and margin near Red-Purple 63C and 63D, both colors present. Veins throughout near Yellow-Green 145B. Outer surface: Petal base near Yellow 10D, rest of petal near Red 56B. Vein coloration near Yellow-Green 145B. Flower throat (inside): Near Yellow 4A, vein coloration near Yellow-Green 145C. Flower tube (outside): Near Yellow-Green 150C, vein coloration near Yellow-Green 145B. Petal color, fading to: Near RHS Yellow 11B, petals and margin near Red-Purple 62D.

Calyx/sepals:
- *Quantity per flower.*—5, fused at base.
- *Shape.*—Oblong.
- *Length.*—Approximately 1.4 cm.
- *Width.*—Approximately 0.3 cm.
- *Apex.*—Acute.

*Base.*—Fused.
*Margin.*—Entire.
*Texture.*—Pubescent, all surfaces.
*Color.*—Upper Surface: Near RHS Green 138A. Lower Surface: Near RHS Green 138A.

Peduncle:
*Length.*—Approximately 2.0 cm.
*Diameter.*—Approximately 0.2 cm.
*Color.*—Near RHS Green 138A.
*Orientation.*—Approximately 25 degree angle from stem. Very slight undulation.

Fragrance: Faint, musty.

REPRODUCTIVE ORGANS

Stamens:
*Number.*—5.
*Filament length.*—Approximately 1.0 to 1.3 cm.

Anthers:
*Length.*—Approximately 0.1 cm.
*Shape.*—Globular.
*Color.*—RHS Green-White N157B.
*Pollen.*—Not observed.

Pistil:
*Number.*—1.
*Length.*—Approximately 1.9 cm.
*Style.*—Length: Approximately 1.6 cm. Color: Near RHS Yellow-Green 145B.
*Stigma.*—Shape: Oblate. Color: Near RHS Green 143C. Ovary Color: Near RHS Green 143C.

OTHER CHARACTERISTICS

Seeds and fruits: Not observed.

Disease/pest resistance: Neither resistant nor susceptible to normal diseases and pests of *Petunia*.

Temperature tolerance: The new variety tolerates temperatures between approximately 6° C. to 35° C.

What is claimed is:

1. A new and distinct cultivar of *Petunia* plant named 'PBLYG39-0' as herein illustrated and described.

* * * * *